US012051207B2

(12) United States Patent
Zhou et al.

(10) Patent No.: US 12,051,207 B2
(45) Date of Patent: Jul. 30, 2024

(54) METHOD, APPARATUS, STORAGE MEDIUM AND PROCESSOR FOR MEDICAL IMAGE AUTO-SEGMENTATION

(71) Applicants: MANTEIA TECHNOLOGIES CO., LTD., Fujian (CN); Shandong cancer hospital affiliate to Shandong University, Shandong (CN)

(72) Inventors: Qichao Zhou, Fujian (CN); Yong Yin, Shandong (CN); Wei Zhang, Fujian (CN); Zhaocai Chen, Fujian (CN)

(73) Assignees: MANTEIA TECHNOLOGIES CO., LTD., Fujian (CN); Shandong cancer hospital affiliate to Shandong University, Jinan (CN)

( * ) Notice: Subject to any disclaimer, the term of this patent is extended or adjusted under 35 U.S.C. 154(b) by 342 days.

(21) Appl. No.: 17/567,921

(22) Filed: Jan. 4, 2022

(65) Prior Publication Data
US 2023/0015384 A1    Jan. 19, 2023

(30) Foreign Application Priority Data
Jul. 14, 2021  (CN) .......................... 202110796442.1

(51) Int. Cl.
*G06T 7/12* (2017.01)
*G06N 3/08* (2023.01)
(Continued)

(52) U.S. Cl.
CPC ................ *G06T 7/12* (2017.01); *G06N 3/08* (2013.01); *G06T 7/0012* (2013.01); *G16H 20/40* (2018.01);
(Continued)

(58) Field of Classification Search
CPC ......... G06T 7/12; G06T 7/0012; G16H 20/40; G16H 30/40; G06N 3/08
See application file for complete search history.

(56) References Cited

U.S. PATENT DOCUMENTS

2017/0213339 A1\* 7/2017 Hibbard ................. G06T 7/143
2019/0050982 A1   2/2019 Song et al.
(Continued)

FOREIGN PATENT DOCUMENTS

CN     108367161 A    8/2018
CN     108447551 A    8/2018
(Continued)

OTHER PUBLICATIONS

The first search report of family CN application No. 2021107964421 issue on Apr. 21, 2023.
(Continued)

*Primary Examiner* — David Bilodeau
(74) *Attorney, Agent, or Firm* — Samson G. Yu

(57) ABSTRACT

The present application discloses a method, an apparatus, a storage medium and a processor for medical image auto-segmentation. The method includes: acquiring a medical image scan of the day of a target patient, wherein the medical image scan of the day is a medical image scanned before the Nth time treatment of the target patient, and N is a natural number greater than 1; performing auto-segmentation on the medical image scan of the day by using a target model to obtain a segmentation result, wherein the target model is a model generated after iterative training based on all images along with the contours from previous N times fractions of the target patient, segmentation result is used to generate the contour for the target treatment plan; and generating the contour for the target treatment plan based on a segmentation result.

9 Claims, 1 Drawing Sheet

(51) Int. Cl.
    *G06T 7/00*     (2017.01)
    *G16H 20/40*    (2018.01)
    *G16H 30/40*    (2018.01)

(52) U.S. Cl.
    CPC ... *G16H 30/40* (2018.01); *G06T 2207/20081* (2013.01); *G06T 2207/20084* (2013.01)

(56) References Cited

U.S. PATENT DOCUMENTS

| | | | | |
|---|---|---|---|---|
| 2020/0104695 | A1* | 4/2020 | Laaksonen | G16H 50/70 |
| 2020/0360728 | A1* | 11/2020 | Tilly | A61N 5/1081 |
| 2021/0090694 | A1* | 3/2021 | Colley | G16H 15/00 |
| 2022/0180524 | A1* | 6/2022 | Novosad | A61N 5/1038 |
| 2022/0296344 | A1* | 9/2022 | Lee | G16H 30/40 |
| 2023/0274438 | A1* | 8/2023 | Chang | G06T 7/0016 |
| | | | | 382/128 |

FOREIGN PATENT DOCUMENTS

| | | |
|---|---|---|
| CN | 108717866 A | 10/2018 |
| CN | 109615642 A | 4/2019 |
| CN | 111784705 A | 10/2020 |

OTHER PUBLICATIONS

The Supplementary search report of family CN application No. 2021107964421 issue on Oct. 18, 2023.

\* cited by examiner

METHOD, APPARATUS, STORAGE MEDIUM AND PROCESSOR FOR MEDICAL IMAGE AUTO-SEGMENTATION

TECHNICAL FIELD

The present application relates to a technical field of image processing, and in particular to a method, an apparatus, a storage medium and a processor for medical image auto-segmentation.

BACKGROUND

Radiotherapy is one of three clinical tumor treatment means at present. Modern radiotherapy has a set of complete treatment procedures, which mainly include auto-segmentation of an organ at risk and a target area, formulation of a radiotherapy plan according to a dosimetry principle, plan implementation and the like, wherein the auto-segmentation of the target area and the organ at risk have a crucial influence on the accuracy and the curative effect of the radiotherapy, and directly determines the accuracy degree of the radiotherapy plan. At present, the auto-segmentation work of the target area and the organ at risk is usually completed manually by doctors and physicians, which greatly wastes the time and energy of the doctors and physicians. More importantly, in current radiotherapy procedures, the auto-segmentation work is usually done only before a first time treatment, and each subsequent treatment is evaluated and implemented after rigid registration by using a first treatment plan as a template in combination with a current day image of a patient. This way is not adaptable to dose implementation due to small displacements and volume changes occurring to the organs in the patient each day. To solve the problem magnetic resonance imaging (MR) is used as a guide, flexible registration is performed on the ROI of the first treatment plan and the ROI of the current day image before each treatment, and it is necessary to delineate the complete ROI of the target area and the organ at risk on the current day image in advance, so as to realize accurate adaptive radiotherapy in a related art. The same planning procedure can also be applied to a CBCT-guided linear accelerator, but the process of auto-segmentation, registration and evaluation of this procedure is too time-consuming to be applied in a large scale clinically at present.

In recent years, due to the rapid development of a deep learning method, image segmentation algorithms based on deep learning have made remarkable achievements in the field of medical image segmentation. Deep learning is a series of algorithms in the field of machine learning that attempt to use multiple nonlinear transformations to perform multi-layer abstraction of data, not only the nonlinear mapping between input and output is learned, but a hidden structure of an input data vector is also learned for performing intelligent identification or prediction on a new sample. The image segmentation algorithms of deep learning have been widely used in automatic auto-segmentation, however, most of the algorithms or models are established based on a larger database, and output auto-segmentation effects and rules are usually homologous with the data and labels in the database, but lack personalized data features of each patient. The auto-segmentation of adaptive radiotherapy requires that it accurately grasp the personalized features of each patient to adjust the treatment plan of the patient in time. Moreover, due to the machine settings for different patients in the related art, and the physical conditions of different patients and environmental interference, it is difficult to construct a model with sufficiently good adaptability and generalization ability by using the deep learning method. At the same time, after the model is deployed, it is impossible to make corresponding algorithm adjustments based on the current day image of each patient.

At present, there is no effective solution provided to solve the problem of worse accuracy in delineating medical images during radiotherapy in the related art yet.

SUMMARY

The main purpose of the present application is to provide a method, an apparatus, a storage medium and a processor for medical image auto-segmentation, so as to solve the problem of worse accuracy in auto-segmentation medical images during radiotherapy.

In order to achieve the above purpose, according to one aspect of the present application, an auto-segmentation method for medical image is provided. The method includes: acquiring a medical image scan of the day of a target patient, wherein the medical image scan of the day is a medical image scanned before the Nth time treatment of the target patient, and N is a natural number greater than 1; performing auto-segmentation on the medical image scan of the day by using a target model to obtain a segmentation result, wherein the target model is a model generated after iterative training based on all images along with the contours from previous N times fractions of the target patient, the segmentation result is used to generate the contour for the target treatment plan.

Further, before performing auto-segmentation on the medical image scan of the day by using the target model, the method further includes: acquiring a first medical image and a first treatment plan of the target patient, wherein the first medical image is the image scanned before the first treatment of the target patient, and the first treatment plan has been approved and used for the treatment plan; training a neural network based on the first medical image and the first treatment plan to obtain a first model; acquiring a second medical image of the target patient, wherein the second medical image is the image scanned before the second treatment of the target patient; performing auto-segmentation on the second medical image by using the first model, generating a second treatment plan based on a first auto-segmentation result, and performing update training on the first model by using the second medical image and the second treatment plan to obtain a second model; and acquiring an Nth medical image of the target patient before a subsequent Nth time treatment of the target patient, performing auto-segmentation on the Nth medical image by using an (N−1)th model, generating an Nth treatment plan based on an (N−1)th auto-segmentation result, and performing update training on the (N−1)th model by using the Nth medical image and the Nth treatment plan to obtain the target model.

Further, after acquiring the first medical image and the first treatment plan of the target patient, the method further includes: performing data augmentation on the first medical image and the first treatment plan by using a target method to obtain data after data augmentation, wherein the data after data augmentation is used for training the neural network.

Further, performing data augmentation on the first medical image and the first treatment plan by using the target method to obtain data after data augmentation includes: determining a target augmentation method by performing random sampling on the combination of spatial transforms and intensity transforms, and the probability and amplitude of these transforms in a first epoch of training; augmenting the first medical image and the first treatment plan by using the target augmentation method to obtain a first training sample; training the neural network by using the first training sample, and re-sampling the data augmentation method and then continue the training after the first epoch of training, storing the current model and optimizer state before each subsequent epoch of training, suspending this epoch of training when it is detected during the training process that the loss is greater than a preset threshold, starting the training from the model and optimizer state stored previous after re-sampling the data augmentation method, and repeating this process until the training is completed to obtain the first model.

Further, before training the neural network based on the first medical image and the first treatment plan to obtain the first model, the method further includes: acquiring a collection of medical images with different modalities of the target patient; and using the a collection of medical images with different modalities as a training set, and pre-training a preset number of epoch by contrastive learning or image reconstruction to obtain a pretrained model, wherein the pretrained model is used to initialize the first target model.

Further, performing auto-segmentation on the second medical image by using the first model, and generating the second treatment plan based on the first auto-segmentation result includes: detecting whether a modification instruction of the target object is received; and performing modification and adjustment on the first auto-segmentation result, and generating the second treatment plan based on the adjusted first auto-segmentation result when the modification instruction of the target object is received in response to the modification instruction; or, detecting whether a confirmation instruction of the target object is received; and generating the second treatment plan by directly using the first auto-segmentation result when the confirmation instruction of the target object is received in response to the confirmation instruction.

Further, the method further includes: storing the medical image and the treatment plan of the target patient during each time in a modeling database to serve as training data for updating the target model.

In order to achieve the above purpose, according to another aspect of the present application, an auto-segmentation apparatus for medical image is provided. The apparatus includes: a first acquisition unit, configured to acquire a medical image scan of the day of a target patient, wherein the medical image scan of the day is a medical image scanned before the Nth time treatment of the target patient, and N is a natural number greater than 1; a first processing unit, configured to perform auto-segmentation on the medical image scan of the day by using a target model to obtain a segmentation result, wherein the target model is a model generated after iterative training based on all images along with the contours from previous N times fractions of the target patient, the segmentation result is used to generate the contour for the target treatment plan.

Further, the apparatus further includes: a second acquisition unit configured to acquire a first medical image and a first treatment plan of the target patient before performing auto-segmentation on the medical image scan of the day by using the target model, wherein the first medical image is the image scanned before the first treatment of the target patient, and the first treatment plan has been approved and used for the treatment plan; a first training unit, configured to train a neural network based on the first medical image and the first treatment plan to obtain a first model; a third acquisition unit, configured to acquire a second medical image of the target patient, wherein the second medical image is the image scanned before the second treatment of the target patient; a fourth acquisition unit, configured to perform auto-segmentation on the second medical image by using the first model, generate a second treatment plan based on a first auto-segmentation result, and perform update training on the first model by using the second medical image and the second treatment plan to obtain a second model; and a fifth acquisition unit configured to acquire an Nth medical image of the target patient, perform auto-segmentation on the Nth medical image by using an (N−1)th model before a subsequent Nth time treatment of the target patient, generate an Nth treatment plan based on an (N−1)th auto-segmentation result, and perform update training on the (N−1)th model by using the Nth medical image and the Nth treatment plan to obtain the target model.

Further, the apparatus further includes: a sixth acquisition unit configured to, after acquiring the first medical image and the first treatment plan of the target patient, perform data augmentation on the first medical image and the first treatment plan by using a target method to obtain data after data augmentation, wherein the data after data augmentation is used for training the neural network.

Further, the sixth acquisition unit includes: a first determination module configured to determine a target augmentation method by perform random sampling on the combination of spatial transforms and intensity transforms, and the probability and amplitude of the data augmentation these transforms in a first epoch of training; a first training module, configured to augment the first medical image and the first treatment plan by using the target augmentation method to obtain a first training sample; a second training module, configured to train the neural network by using the first training sample, and a first processing module configured to re-sample the data augmentation method and then continue the training after the first epoch of training, store the current model and optimizer state before each subsequent epoch of training, suspend this epoch of training when it is detected during the training process that the loss is greater than a preset threshold start the training from the model and optimizer state stored previous after re-sample the data augmentation method, and repeat this process until the training is completed to obtain the first model.

Further, the apparatus further includes: a seventh acquisition unit configured to acquire a collection of medical images with different modalities of the target patient before training the neural network based on the first medical image and the first treatment plan to obtain the first model; and a second training unit, configured to use the a collection of medical images with different modalities as a training set, and perform pre-training for a preset number of epoch by contrastive learning or image reconstruction to obtain a pretrained model, wherein the pretrained model is used for initializing the first medical image and the first treatment plan.

Further, the fourth acquisition unit includes: a first detection module, configured to detect whether a modification instruction of the target object is received; and a first response module configured to, if the modification instruction of the target object is received, in response to the modification instruction, perform modification and adjustment on the first auto-segmentation result, and generate the second treatment plan based on the adjusted first auto-segmentation result; or, a second detection module, configured to detect whether a confirmation instruction of the target object is received; and a second response module configured to, when the confirmation instruction of the target object is received, in response to the confirmation instruction, generate the second treatment plan by directly using the first auto-segmentation result.

Further, the apparatus further includes: a first updating unit, configured to store the medical image and the treatment plan of the target patient during each time in a modeling database to serve as training data for updating the target model.

According to another aspect of the embodiment of the present application, a processor is further provided. The processor is used for running a program, wherein the program executes any one of the above-mentioned methods while running.

According to another aspect of the embodiment of the present application, a computer-readable storage medium is further provided, on which a computer program/instruction is stored, and when executed by a processor, the computer program/instruction executes any one of the above-mentioned methods.

By means of the present application, the following steps are adopted: acquiring a medical image scan of the day of a target patient, wherein the medical image scan of the day is a medical image scanned before the Nth time treatment of the target patient, and N is a natural number greater than 1; performing auto-segmentation on the medical image scan of the day by using a target model to obtain a segmentation result, wherein the target model is a model generated after iterative training based on all images along with the contours from previous N times fractions of the target patient, the segmentation result is used to generate the contour for the target treatment plan. By means of the present application, the problem of worse accuracy in segmenting medical images during radiotherapy is solved. The medical image of the target patient is delineated by using the model trained for the medical image and the treatment plan of the target patient during each time, therefore, the personalized features of the target patient are taken into account, thereby improving the effect of medical image segmentation accuracy.

BRIEF DESCRIPTION OF THE DRAWINGS

The drawings constituting a part of the present application are used for providing a further understanding of the present application, and the exemplary embodiments of the present application and descriptions thereof are used for explaining the present application, but do not constitute improper limitations of the present application. In the drawings.

DETAILED DESCRIPTION OF THE EMBODIMENTS

It should be noted that, the embodiments in the present application and the features in the embodiments can be combined with each other if there is no conflict. Hereinafter, the present application will be described in detail with reference to the drawings and in conjunction with the embodiments.

In order to make those skilled in the art better understand the solutions of the present application, a clear and complete description of technical solutions in the embodiments of the present application will be given below, in combination with the drawings in the embodiments of the present application. Apparently, the embodiments described below are merely a part, but not all, of the embodiments of the present application. All of other embodiments, obtained by those of ordinary skill in the art based on the embodiments in the present application without any creative effort, shall all fall into the protection scope of the present application.

It should be noted that, the terms "first" and "second" and the like in the description and the claims of the present application and the above-mentioned drawings are used for distinguishing similar objects, and are not necessarily used for describing a specific sequence or order. It should be understood that the data used in this way can be interchanged under appropriate circumstances to describe the embodiments of the present application. In addition, the terms "including" and "having" and any variations thereof are intended to cover non-exclusive inclusions, for example, processes, methods, systems, products, or devices that include a series of steps or units are not necessarily limited to those clearly listed steps or units, but can include other steps or units that are not clearly listed or are inherent to these processes, methods, products, or devices.

According to an embodiment of the present application, an auto-segmentation method for medical image is provided.

Figure 1:
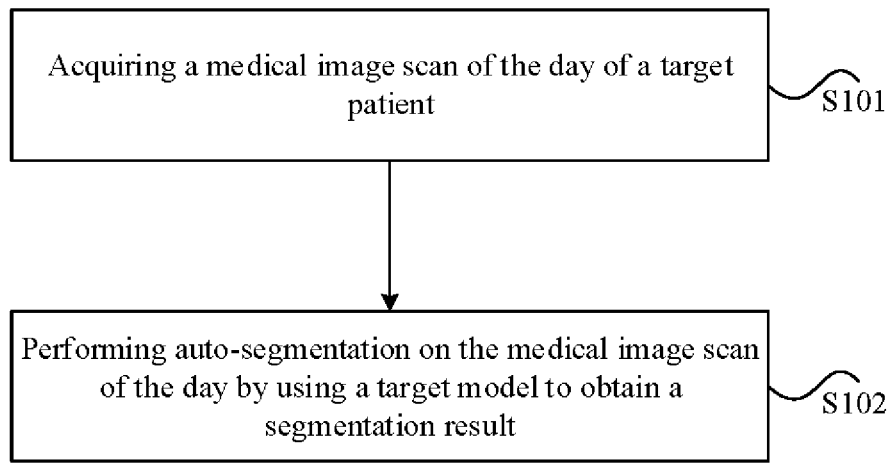
FIG. 1 is a flow diagram of an auto-segmentation method for medical image provided according to an embodiment of the present application.

FIG. 1 is a flow diagram of an auto-segmentation method for medical image provided according to an embodiment of the present application. As shown in FIG. 1, the method includes the following steps:

Step S101, acquiring a medical image scan of the day of a target patient, wherein the medical image scan of the day is a medical image scanned before the Nth time treatment of the target patient, and N is a natural number greater than 1.

The above-mentioned medical image can be a magnetic resonance image MR or a cone beam CT image, which is not limited in the present application.

For example, a patient A prepares for the 10th treatment on Jun. 1, 2021. The medical image of the patient A taken on Jun. 1, 2021 is acquired. It should be noted that, the above-mentioned current day medical image is not necessarily limited to a medical image scanned on the day of treatment, and can also be a medical image scanned recently.

Step S102, performing auto-segmentation on the medical image scan of the day by using a target model to obtain a segmentation result, wherein the target model is a model generated after iterative training based on all images along with the contours from previous N times fractions of the target patient, the segmentation result is used to generate the contour for the target treatment plan.

For example, the target model is a model generated after iterative training based on a medical image and a treatment plan of the target patient during each time of the previous 9 times, the medical image scan of the day is delineated. That is, the target model is a model trained based on personalized features of the target patient. Since the personalized data features of the patient are taken into account, the segmentation result is more accurate. As the segmentation result is more accurate, the personalized features of each patient can be accurately grasped, and then the treatment plan of the patient can be adjusted in time, thereby ensuring that the generated target treatment plan can make the treatment of the patient be more accurate.

Optionally, in the auto-segmentation method for the medical image provided by the embodiment of the present application, before performing auto-segmentation on the medical image scan of the day by using the target model, the method further includes: acquiring a first medical image and a first treatment plan of the target patient, wherein the first medical image is the image scanned before the first treatment of the target patient, and the first treatment plan has been approved and used for the treatment plan; training a neural network based on the first medical image and the first treatment plan to obtain a first model; acquiring a second medical image of the target patient, wherein the second medical image is the image scanned before the second treatment of the target patient; performing auto-segmentation on the second medical image by using the first model, generating a second treatment plan based on a first auto-segmentation result, and performing update training on the first model by using the second medical image and the second treatment plan to obtain a second model; acquiring an Nth medical image of the target patient before a subsequent Nth time treatment of the target patient, performing auto-segmentation on the Nth medical image by using an (N−1)th model, and generating an Nth treatment plan based on an (N−1)th auto-segmentation result; and performing update training on the (N−1)th model by using the Nth medical image and the Nth treatment plan to obtain the target model.

The above-mentioned neural network can be a U-Net convolutional neural network. By means of the above-mentioned solution, the model can be updated according to the medical image and treatment plan of the treatment of the target patient to ensure the accuracy and precision of the obtained target model. Therefore, except that the first time treatment plan of the target patient is a treatment plan determined by a doctor by segmenting the medical image of the first time, the medical image of each subsequent treatment of the patient can be determined from the treatment plan of the previous treatment and the model obtained from medical image learning and training, and the current medical image for treatment is delineated, so that the segmentation result is more accurate.

Optionally, in the auto-segmentation method for the medical image provided by the embodiment of the present application, after acquiring the first medical image and the first treatment plan of the target patient, the method further includes: performing data augmentation on the first medical image and the first treatment plan by using a target method to obtain data after data augmentation, wherein the data after data augmentation is used for training the neural network.

Specifically, performing data augmentation on the first medical image and the first treatment plan by using the target method to obtain the data after data augmentation includes: determining a target augmentation method by performing random sampling on the combination of spatial transforms and intensity transforms, and the probability and amplitude of these transforms in a first epoch of training; augmenting the first medical image and the first treatment plan by using the target augmentation method to obtain a first training sample; training the neural network by using the first training sample, and re-sampling the data augmentation method and then continue the training after the first epoch of training, storing the current model and optimizer state before each subsequent epoch of training, suspending this epoch of training when it is detected during the training process that the loss is greater than a preset threshold, starting the training from the model and optimizer state stored previous after re-sampling the data augmentation method, and repeating this process until the training is completed to obtain the first model.

In the above solution, the combination, probability and amplitude of the data augmentation are determined by random sampling. For example, the augmentation methods are sampled before the start of training, that is, one or more augmentation methods are randomly selected for combination, and the probability and magnitude of augmentation are randomly determined. After a epoch of training (for example, 100 iterations are performed in each epoch), the augmentation methods are re-sampled and then are trained again. The current model and optimizer state is saved before the start of each epoch of training, when the loss increases significantly during the training process and reaches the preset threshold (that is, the data loss amplitude is greater than the preset amplitude, and the data loss value is greater than the preset threshold), this epoch of training is suspended, the training is started from the model and optimizer state saved last time after re-sampling, and this process is repeated until the training is completed.

By means of the above solution, the accuracy of the model in the case of very small training samples can be effectively improved. In addition, in the subsequent process of training the second model, the third model . . . the target model, the above solution can be used for performing augmentation processing on the training data in each epoch to ensure the accuracy and precision of the obtained model.

Optionally, in the auto-segmentation method for the medical image provided by the embodiment of the present application, before training the neural network based on the first medical image and the first treatment plan to obtain the first model, the method further includes: acquiring a collection of medical images with different modalities of the target patient; and using the a collection of medical images with different modalities as a training set, and performing pre-training for a preset number of epoch by contrastive learning or image reconstruction to obtain a pretrained model, wherein the pretrained model is used for initializing the first medical image and the first treatment plan.

For example, data of a large number of medical images with different modalities (including, but not limited to CT, T1, T2 and T2 augmentation) are used as the training set, multiple epochs (for example, 1000 epochs) of pre-training are performed in the way of comparison learning or image restoration to obtain the pretrained model, and the pretrained model can be used for initializing the first medical image and the first treatment plan, thereby improving the accuracy of the subsequently trained target model.

In addition, the model completed in the last training of the target patient is also used as the pretrained model to initialize the current medical image and the current treatment plan of the patient, which can also improve the accuracy of the subsequently trained target model.

Optionally, in the auto-segmentation method for the medical image provided by the embodiment of the present application, performing auto-segmentation on the second medical image by using the first model, and generating the second treatment plan based on the first auto-segmentation result includes: detecting whether a modification instruction of the target object is received; and performing modification and adjustment on the first auto-segmentation result, and generating the second treatment plan based on the adjusted first auto-segmentation result when the modification instruction of the target object is received in response to the modification instruction; or, detecting whether a confirmation instruction of the target object is received; and generating the second treatment plan by directly using the first auto-segmentation result when the confirmation instruction of the target object is received in response to the confirmation instruction.

In the above solution, for the accuracy of the segmentation of the medical image, the doctor or physicist (corresponding to the above target object) can actively modify the auto-segmentation result, or confirm the auto-segmentation result to ensure the accuracy of the auto-segmentation result, and then, the treatment plan can be accurately generated according to the auto-segmentation result.

Optionally, in the auto-segmentation method for the medical image provided by the embodiment of the present application, the method further includes: storing the medical image and the treatment plan of the target patient during each time in a modeling database to serve as training data for updating the target model.

For example, the current day image and the current day treatment plan of the first time treatment of the target patient are added into the modeling database, and a deep learning model is constructed and trained to serve as the first model. Before the second time treatment of the patient, the current day image is acquired, the current day image is automatically delineated by using the first model, and the doctor or physicist completes the modification and confirmation of the segmentation, and adds the confirmed image and plan into the modeling database. After the database is updated, a new epoch of model training is performed, and the latest model is used as the current model. This step is fully automated. During each subsequent treatment, the above process will be repeated to continuously update the database and train the data. In addition, it should be noted that the process of adding the medical image and the treatment plan of the target patient during each time into the modeling database is fully automated, and no user intervention is required.

The auto-segmentation method for the medical image provided by the embodiment of the present application includes: acquiring a medical image scan of the day of a target patient, wherein the medical image scan of the day is a medical image scanned before the Nth time treatment of the target patient, and N is a natural number greater than 1; performing auto-segmentation on the medical image scan of the day by using a target model to obtain a segmentation result, wherein the target model is a model generated after iterative training based on all images along with the contours from previous N times fractions of the target patient, the segmentation result is used to generate the contour for the target treatment plan. By means of the present application, the problem of worse accuracy in segmenting medical images during radiotherapy is solved. The medical image of the target patient is delineated by using the model trained for the medical image and the treatment plan of the target patient during each time, therefore, the personalized features of the patient are taken into account, thereby improving the effect of medical image segmentation accuracy.

It should be noted that, the steps shown in the flow diagram of the drawings can be executed in a computer system such as a set of computer-executable instructions, and although a logical sequence is shown in the flow diagram, in some cases, the steps shown or described can be performed in a different sequence than here.

The embodiment of the present application further provides an auto-segmentation apparatus for medical image. It should be noted that the auto-segmentation apparatus for the medical image in the embodiment of the present application can be used for implementing the auto-segmentation method for the medical image. The auto-segmentation apparatus for the medical image provided in the embodiment of the present application will be described below.

Figure 2:
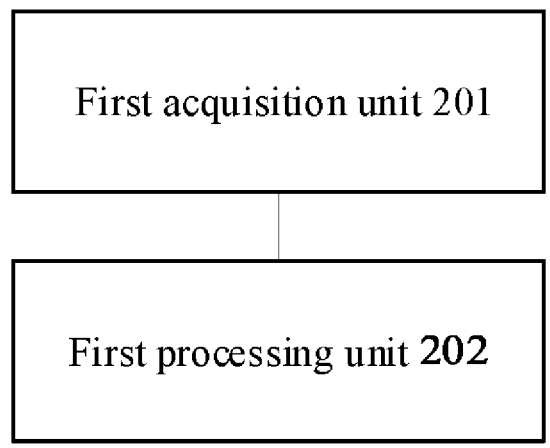
FIG. 2 is a schematic diagram of an auto-segmentation apparatus for medical image provided according to an embodiment of the present application.

FIG. 2 is a schematic diagram of an auto-segmentation apparatus for medical image provided according to an embodiment of the present application. As shown in FIG. 2, the apparatus includes: a first acquisition unit 201, a first processing unit 202.

Specifically, the first acquisition unit 201 is configured to acquire a medical image scan of the day of a target patient, wherein the medical image scan of the day is a medical image scanned before the Nth time treatment of the target patient, and N is a natural number greater than 1.

The first processing unit 202 is configured to perform auto-segmentation on the medical image scan of the day by using a target model to obtain a segmentation result, wherein the target model is a model generated after iterative training based on all images along with the contours from previous N times fractions of the target patient, the segmentation result is used to generate the contour for the target treatment plan. In summary, according to the auto-segmentation apparatus for the medical image, the first acquisition unit 201 acquires a medical image scan of the day of a target patient, wherein the medical image scan of the day is a medical image scanned before the Nth time treatment of the target patient, and N is a natural number greater than 1; the first processing unit performs auto-segmentation on the medical image scan of the day by using a target model to obtain a segmentation result, wherein the target model is a model generated after iterative training based on all images along with the contours from previous N times fractions of the target patient, the segmentation result is used to generate the contour for the target treatment plan. The problem of worse accuracy in segmenting medical images during radiotherapy is solved. The medical image of the target patient is delineated by using the model trained for the medical image and the treatment plan of the target patient during each time, therefore, the personalized features of the patient are taken into account, thereby improving the effect of medical image segmentation accuracy.

Optionally, in the auto-segmentation apparatus for the medical image provided by the embodiment of the present application, the apparatus further includes: a second acquisition unit configured to acquire a first medical image and a first treatment plan of the target patient before performing auto-segmentation on the medical image scan of the day by using the target model, wherein the first medical image is the image scanned before the first treatment of the target patient, and the first treatment plan has been approved and used for the treatment plan; a first training unit, configured to train a neural network based on the first medical image and the first treatment plan to obtain a first model; a third acquisition unit, configured to acquire a second medical image of the target patient, wherein the second medical image is the image scanned before the second treatment of the target patient; a fourth acquisition unit, configured to perform auto-segmentation on the second medical image by using the first model, generate a second treatment plan based on a first auto-segmentation result, and perform update training on the first model by using the second medical image and the second treatment plan to obtain a second model; and a fifth acquisition unit configured to acquire an Nth medical image of the target patient, perform auto-segmentation on the Nth medical image by using an (N−1)th model before a subsequent Nth time treatment of the target patient, generate an Nth treatment plan based on an (N−1)th auto-segmentation result, and perform update training on the (N−1)th model by using the Nth medical image and the Nth treatment plan to obtain the target model.

Optionally, in the auto-segmentation apparatus for the medical image provided by the embodiment of the present application, the apparatus further includes: a sixth acquisition unit configured to perform data augmentation on the first medical image and the first treatment plan by using a target method after acquiring the first medical image and the first treatment plan of the target patient to obtain data after data augmentation, wherein the data after data augmentation is used for training the neural network.

Optionally, in the auto-segmentation apparatus for the medical image provided by the embodiment of the present application, the sixth acquisition unit includes: a first determination module configured to determine a target augmentation method by perform random sampling on the combination of spatial transforms and intensity transforms, and the probability and amplitude of the data augmentation these transforms in a first epoch of training; a first augmenting module, configured to augment the first medical image and the first treatment plan by using the target augmentation method to obtain a first training sample; a second training module, configured to train the neural network by using the first training sample, and a first processing module configured to re-sample the data augmentation method and then continue the training after the first epoch of training, store the current model and optimizer state before each subsequent epoch of training, suspend this epoch of training when it is detected during the training process that the loss is greater than a preset threshold, start the training from the model and optimizer state stored previous after re-sample the data augmentation method, and repeat this process until the training is completed to obtain the first model.

Optionally, in the auto-segmentation apparatus for the medical image provided by the embodiment of the present application, the apparatus further includes: a seventh acquisition unit configured to, before training the neural network based on the first medical image and the first treatment plan to obtain the first model, acquire a collection of medical images with different modalities of the target patient; and a second training unit, configured to use a collection of medical images with different modalities as a training set, and perform pre-training for a preset number of epoch by contrastive learning or image reconstruction to obtain a pretrained model, wherein the pretrained model is used for initializing the first medical image and the first treatment plan.

Optionally, in the auto-segmentation apparatus for the medical image provided by the embodiment of the present application, the fourth acquisition unit includes: a first detection module, configured to detect whether a modification instruction of the target object is received; and a first response module configured to, if the modification instruction of the target object is received, in response to the modification instruction, perform modification and adjustment on the first auto-segmentation result, and generate the second treatment plan based on the adjusted first auto-segmentation result; or, a second detection module, configured to detect whether a confirmation instruction of the target object is received; and a second response module configured to, if the confirmation instruction of the target object is received, in response to the confirmation instruction, generate the second treatment plan by directly using the first auto-segmentation result.

Optionally, in the auto-segmentation apparatus for the medical image provided by the embodiment of the present application, the apparatus further includes: a first updating unit, configured to store the medical image and the treatment plan of the target patient during each time in a modeling database to serve as training data for updating the target model.

The auto-segmentation apparatus for the medical image includes a processor and a memory, the first acquisition unit 201, the first processing unit 202 are all stored in the memory as program units, and the processor executes the above program units stored in the memory to realize corresponding functions.

The processor includes a kernel, and the kernel calls the corresponding program unit from the memory. One or more kernels can be set, and the medical image is delineated by adjusting kernel parameters.

The memory may include a volatile memory, a random access memory (RAM) and/or a non-volatile memory and other forms in a computer-readable medium, such as a read-only memory (ROM) or a flash memory (flash RAM), and the memory includes at least one storage chip.

The embodiment of the present invention provides a storage medium, on which a program is stored, and when executed by a processor, the program implements an auto-segmentation method for medical image.

The embodiment of the present invention provides a processor, which is used for running a program, wherein the program implements an auto-segmentation method for medical image while running.

The embodiment of the present invention provides a device, including a processor, a memory, and a program stored on the memory and capable of running on the processor, wherein the processor implements the following steps when executing the program: acquiring a medical image scan of the day of a target patient, wherein the medical image scan of the day is a medical image scanned before the Nth time treatment of the target patient, and N is a natural number greater than 1; performing auto-segmentation on the medical image scan of the day by using a target model to obtain a segmentation result, wherein the target model is a model generated after iterative training based on all images along with the contours from previous N times fractions of the target patient, the segmentation result is used to generate the contour for the target treatment plan.

The processor also implements the following steps when executing the program: acquiring a first medical image and a first treatment plan of the target patient before performing auto-segmentation on the medical image scan of the day by using the target model, wherein the first medical image is the image scanned before the first treatment of the target patient, and the first treatment plan has been approved and used for the treatment plan; training a neural network based on the first medical image and the first treatment plan to obtain a first model; acquiring a second medical image of the target patient, wherein the second medical image is the image scanned before the second treatment of the target patient; performing auto-segmentation on the second medical image by using the first model, generating a second treatment plan based on a first auto-segmentation result, and performing update training on the first model by using the second medical image and the second treatment plan to obtain a second model; and acquiring an Nth medical image of the target patient before a subsequent Nth time treatment of the target patient, performing auto-segmentation on the Nth medical image by using an (N−1)th model, generating an Nth treatment plan based on an (N−1)th auto-segmentation result, and performing update training on the (N−1)th model by using the Nth medical image and the Nth treatment plan to obtain the target model.

The processor also implements the following steps when executing the program: after acquiring the first medical image and the first treatment plan of the target patient, performing data augmentation on the first medical image and the first treatment plan by using a target method to obtain data after data augmentation, wherein the data after data augmentation is used for training the neural network.

The processor also implements the following steps when executing the program: determining a target augmentation method by performing random sampling on the combination of spatial transforms and intensity transforms, and the probability and amplitude of these transforms in a first epoch of training; augmenting the first medical image and the first treatment plan by using the target augmentation method to obtain a first training sample; training the neural network by using the first training sample, and re-sampling the data augmentation method and then continue the training after the first epoch of training, storing the current model and optimizer state before each subsequent epoch of training, suspending this epoch of training when it is detected during the training process that the loss is greater than a preset threshold, starting the training from the model and optimizer state stored previous after re-sampling the data augmentation method, and repeating this process until the training is completed to obtain the first model.

The processor also implements the following steps when executing the program: acquiring a collection of medical images with different modalities of the target patient before training the neural network based on the first medical image and the first treatment plan to obtain the first model; and using a collection of medical images with different modalities as a training set, and pre-training a preset number of epoch by contrastive learning or image reconstruction to obtain a pretrained model, wherein the pretrained model is used to initialize the first target model.

The processor also implements the following steps when executing the program: detecting whether a modification instruction of the target object is received; and performing modification and adjustment on the first auto-segmentation result, and generating the second treatment plan based on the adjusted first auto-segmentation result when the modification instruction of the target object is received in response to the modification instruction; or, detecting whether a confirmation instruction of the target object is received; and generating the second treatment plan by directly using the first auto-segmentation result when the confirmation instruction of the target object is received in response to the confirmation instruction.

The processor also implements the following steps when executing the program: storing the medical image and the treatment plan of the target patient during each time in a modeling database to serve as training data for updating the target model.

The device in this article can be a server, a PC, a PAD, a mobile phone, etc.

The present application further provides a computer program product, which when executed on a data processing device, is suitable for initializing a program with the following method steps: acquiring a medical image scan of the day of a target patient, wherein the medical image scan of the day is a medical image scanned before the Nth time treatment of the target patient, and N is a natural number greater than 1; performing auto-segmentation on the medical image scan of the day by using a target model to obtain a segmentation result, wherein the target model is a model generated after iterative training based on all images along with the contours from previous N times fractions of the target patient, the segmentation result is used to generate the contour for the target treatment plan.

When executed on the data processing device, the computer program product is further suitable for initializing a program with the following method steps: acquiring a first medical image and a first treatment plan of the target patient before performing auto-segmentation on the medical image scan of the day by using the target model, wherein the first medical image is the image scanned before the first treatment of the target patient, and the first treatment plan has been approved and used for the treatment plan; training a neural network based on the first medical image and the first treatment plan to obtain a first model; acquiring a second medical image of the target patient, wherein the second medical image is the image scanned before the second treatment of the target patient; performing auto-segmentation on the second medical image by using the first model, generating a second treatment plan based on a first auto-segmentation result, and performing update training on the first model by using the second medical image and the second treatment plan to obtain a second model; and acquiring an Nth medical image of the target patient before a subsequent Nth time treatment of the target patient, performing auto-segmentation on the Nth medical image by using an (N−1)th model, generating an Nth treatment plan based on an (N−1)th auto-segmentation result, and performing update training on the (N−1)th model by using the Nth medical image and the Nth treatment plan to obtain the target model.

When executed on the data processing device, the computer program product is further suitable for initializing a program with the following method steps: after acquiring the first medical image and the first treatment plan of the target patient, performing data augmentation on the first medical image and the first treatment plan by using a target method to obtain data after data augmentation, wherein the data after data augmentation is used for training the neural network.

When executed on the data processing device, the computer program product is further suitable for initializing a program with the following method steps: determining a target augmentation method by performing random sampling on the combination of spatial transforms and intensity transforms, and the probability and amplitude of these transforms in a first epoch of training; augmenting the first medical image and the first treatment plan by using the target augmentation method to obtain a first training sample; training the neural network by using the first training sample, and re-sampling the data augmentation method and then continue the training after the first epoch of training, storing the current model and optimizer state before each subsequent epoch of training, suspending this epoch of training when it is detected during the training process that the loss is greater than a preset threshold, starting the training from the model and optimizer state stored previous after re-sampling the data augmentation method, and repeating this process until the training is completed to obtain the first model.

When executed on the data processing device, the computer program product is further suitable for initializing a program with the following method steps: acquiring a collection of medical images with different modalities of the target patient before training the neural network based on the first medical image and the first treatment plan to obtain the first model; and using a collection of medical images with different modalities as a training set, and pre-training a preset number of epoch by contrastive learning or image reconstruction to obtain a pretrained model, wherein the pretrained model is used to initialize the first target model.

When executed on the data processing device, the computer program product is further suitable for initializing a program with the following method steps: detecting whether a modification instruction of the target object is received; and performing modification and adjustment on the first auto-segmentation result, and generating the second treatment plan based on the adjusted first auto-segmentation result when the modification instruction of the target object is received, in response to the modification instruction; or, detecting whether a confirmation instruction of the target object is received; and generating the second treatment plan by directly using the first auto-segmentation result when the confirmation instruction of the target object is received in response to the confirmation instruction.

When executed on the data processing device, the computer program product is further suitable for initializing a program with the following method steps: storing the medical image and the treatment plan of the target patient during each time in a modeling database to serve as training data for updating the target model.

Those skilled in the art should understand that, the embodiment of the present application can be provided as a method, a system or a computer program product. Accordingly, the present application can adopt the form of a complete hardware embodiment, a complete software embodiment, or an embodiment combining software with hardware. Moreover, the present application can adopt the form of a computer program product which is implemented on one or more computer usable storage media (including, but not limited to, a magnetic disk memory, a CD-ROM and an optical memory and the like) containing computer usable program codes.

The present application is described in accordance with a flow diagram and/or a block diagram of the method, the device (system) and the computer program product in the embodiment of the present application. It should be understood that computer program instructions realize each flow and/or block in the flow diagram and/or the block diagram and the combination of the flows and/or blocks in the flow diagram and/or the block diagram. These computer program instructions can be provided for a general-purpose computer, a special-purpose computer, an embedded processor or processors of other programmable data processing devices to generate a machine, such that the instructions executed by the computers or the processors of the other programmable data processing devices generate apparatuses used for realizing specified functions in one or more flows of the flow diagram and/or one or more blocks of the block diagram.

These computer program instructions can also be stored in a computer readable memory capable of guiding the computers or the other programmable data processing devices to work in particular manners, such that the instructions stored in the computer readable memory generate products including instruction apparatuses, and the instruction apparatuses realize the specified functions in one or more flows of the flow diagram and/or one or more blocks of the block diagram.

These computer program instructions can also be loaded on the computers or the other programmable data processing devices to execute a series of operation steps on the computers or the other programmable data processing devices to produce processing realized by the computers, such that the instructions executed on the computers or the other programmable data processing devices provide steps used for realizing the specified functions in one or more flows of the flow diagram and/or one or more blocks of the block diagram.

In a typical configuration, the computing device includes one or more central processing units (CPU), an input/output interface, a network interface and a memory.

The memory may include a volatile memory, a random access memory (RAM) and/or a non-volatile memory and other forms in a computer-readable medium, such as a read-only memory (ROM) or a flash memory (flash RAM). The memory is an example of the computer-readable medium.

The computer-readable medium includes non-volatile and volatile, and removable and non-removable media, which can realize information storage by means of any method or technology. The information can be computer-readable instructions, data structures, program modules, or other data. Examples of the storage medium of a computer include, but are not limited to, a phase change memory (PRAM), a static random access memory (SRAM), a dynamic random access memory (DRAM), other types of random access memories (RAMs), a read-only memory (ROM), an electrically erasable programmable read-only memory (EEPROM), a flash memory or other memory technologies, a compact disc-read-only memory (CD-ROM), a digital versatile disc (DVD) or other optical memories, a magnetic cassette, a magnetic tape disk memory or other magnetic storage devices or any other non-transmission media, which can be used for storing information that can be accessed by computing devices. According to the definition in this article, the computer-readable medium does not include transitory media (transitory media), such as modulated data signals and carrier waves.

It should also be noted that, the terms "include", "comprise" or any other variants thereof are intended to cover non-exclusive inclusions, such that a process, a method, a commodity or a device including a series of elements not only includes those elements, but also includes other elements that are not explicitly listed, or also includes elements inherent to such a process, method, commodity or device. If there are no more restrictions, the element defined by the sentence "including a . . . " does not exclude the existence of other identical elements in the process, the method, the commodity or the device that includes the element.

Those skilled in the art should understand that, the embodiment of the present application can be provided as a method, a system or a computer program product. Accordingly, the present application can adopt the form of a complete hardware embodiment, a complete software embodiment, or an embodiment combining software with hardware. Moreover, the present application can adopt the form of a computer program product which is implemented on one or more computer usable storage media (including, but not limited to, a magnetic disk memory, a CD-ROM and an optical memory and the like) containing computer usable program codes.

The above descriptions are only embodiments of the present application, and are not intended to limit the present application. For those skilled in the art, the present application can have various modifications and changes. Any modifications, equivalent replacements, improvements and the like, made within the spirit and principle of the present application, shall all be included in the scope of the claims of the present application.

What claimed is:

1. An auto-segmentation method for medical image, comprising:
acquiring a medical image scan of the day of a target patient, wherein the medical image scan of the day is a medical image scanned before the Nth time treatment of the target patient, and N is a natural number greater than 1;

performing auto-segmentation on the medical image scan of the day by using a target model to obtain a segmentation result, wherein the target model is a model generated after iterative training based on all images along with the contours from previous N times fractions of the target patient, the segmentation result is used to generate the contour for the target treatment plan;

wherein before performing auto-segmentation on the medical image scan of the day by using the target model, the method further comprises:

acquiring a first medical image and a first treatment plan of the target patient, wherein the first medical image is the image scanned before the first treatment of the target patient, and the first treatment plan has been approved and used for the treatment plan;

training a neural network based on the first medical image and the first treatment plan to obtain a first model;

acquiring a second medical image of the target patient, wherein the second medical image is the image scanned before the second treatment of the target patient;

performing auto-segmentation on the second medical image by using the first model, generating a second treatment plan based on a first auto-segmentation result, and performing update training on the first model by using the second medical image and the second treatment plan to obtain a second model; and acquiring an Nth medical image of the target patient before a subsequent Nth time treatment of the target patient, performing auto-segmentation on the Nth medical image by using an (N−1)th model, generating an Nth treatment plan based on an (N−1)th auto-segmentation result, and performing update training on the (N−1)th model by using the Nth medical image and the Nth treatment plan to obtain the target model.

2. The method as claimed in claim 1, wherein after acquiring the first medical image and the first treatment plan of the target patient, the method further comprises:

performing data augmentation on the first medical image and the first treatment plan by using a target method to obtain data after data augmentation, wherein the data after data augmentation is used for training the neural network.

3. The method as claimed in claim 2, wherein performing data augmentation on the first medical image and the first treatment plan by using the target method to obtain the data after data augmentation comprises:

determining a target augmentation method by performing random sampling on the combination of spatial transforms and intensity transforms, and the probability and amplitude of these transforms in a first epoch of training;

augmenting the first medical image and the first treatment plan by using the target augmentation method to obtain a first training sample;

training the neural network by using the first training sample, and re-sampling the data augmentation method and then continue the training after the first epoch of training, storing the current model and optimizer state before each subsequent epoch of training, suspending this epoch of training when it is detected during the training process that the loss is greater than a preset threshold, starting the training from the model and optimizer state stored previous after re-sampling the data augmentation method, and repeating this process until the training is completed to obtain the first model.

4. The method as claimed in claim 1, wherein before training the neural network based on the first medical image and the first treatment plan to obtain the first model, the method further comprises:

acquiring a collection of medical images with different modalities of the target patient; and using the a collection of medical images with different modalities as a training set, and pre-training a preset number of epoch by contrastive learning or image reconstruction to obtain a pretrained model, wherein the pretrained model is used to initialize the first target model.

5. The method as claimed in claim 1, wherein performing auto-segmentation on the second medical image by using the first model, and generating the second treatment plan based on the first auto-segmentation result comprises:

detecting whether a modification instruction of the target object is received; and performing modification and adjustment on the first auto-segmentation result, and generating the second treatment plan based on the adjusted first auto-segmentation result when the modification instruction of the target object is received in response to the modification instruction; or;

detecting whether a confirmation instruction of the target object is received; and generating the second treatment plan by directly using the first auto-segmentation result when the confirmation instruction of the target object is received in response to the confirmation instruction.

6. The method as claimed in claim 1, wherein the method further comprises:

storing the medical image and the treatment plan of the target patient during each time in a modeling database to serve as training data for updating the target model.

7. An auto-segmentation apparatus for medical image, comprising:

a first acquisition unit, configured to acquire a medical image scan of the day of a target patient, wherein the medical image scan of the day is a medical image scanned before the Nth time treatment of the target patient, and N is a natural number greater than 1;

a first processing unit, configured to perform auto-segmentation on the medical image scan of the day by using a target model to obtain a segmentation result, wherein the target model is a model generated after iterative training based on all images along with the contours from previous N times fractions of the target patient, segmentation result is used to generate the contour for the target treatment plan;

wherein the apparatus further comprises: a second acquisition unit configured to acquire a first medical image and a first treatment plan of the target patient before performing auto-segmentation on the medical image scan of the day by using the target model, wherein the first medical image is the image scanned before the first treatment of the target patient, and the first treatment plan has been approved and used for the treatment plan; a first training unit, configured to train a neural network based on the first medical image and the first treatment plan to obtain a first model; a third acquisition unit, configured to acquire a second medical image of the target patient, wherein the second medical image is the image scanned before the second treatment of the target patient; a fourth acquisition unit, configured to perform auto-segmentation on the second medical image by using the first model, generate a second treatment plan based on a first auto-segmentation result, and perform update training on the first model by using the second medical image and the second treatment plan to obtain a second model; and a fifth acquisition unit configured to acquire an Nth medical image of the target patient, perform auto-segmentation on the Nth medical image by using an (N−1)th model before a subsequent Nth time treatment of the target patient, generate an Nth treatment plan based on an (N−1)th auto-segmentation result, and perform update training on the (N−1)th model by using the Nth medical image and the Nth treatment plan to obtain the target model.

8. A processor, wherein the processor is used for running a program, and the program executes the method as claimed in claim 1 while running.

9. A non-transitory computer readable medium, wherein the non-transitory computer readable medium comprises a stored program, and the program executes the method as claimed in claim 1.

* * * * *